United States Patent
Plain et al.

(10) Patent No.: US 8,581,211 B2
(45) Date of Patent: Nov. 12, 2013

(54) IMAGING METHOD AND SYSTEM USING SUBSTRATE FUNCTIONALIZATION

(75) Inventors: Jerome Plain, Troyes (FR); Rodolphe Jaffiol, Troyes (FR)

(73) Assignee: Universite de Technologies de Troyes, Troyes Cedex (FR)

( * ) Notice: Subject to any disclaimer, the term of this patent is extended or adjusted under 35 U.S.C. 154(b) by 13 days.

(21) Appl. No.: 13/501,551

(22) PCT Filed: Oct. 13, 2010

(86) PCT No.: PCT/FR2010/052163
§ 371 (c)(1),
(2), (4) Date: Jun. 21, 2012

(87) PCT Pub. No.: WO2011/045530
PCT Pub. Date: Apr. 21, 2011

(65) Prior Publication Data
US 2012/0252056 A1 Oct. 4, 2012

(30) Foreign Application Priority Data
Oct. 13, 2009 (FR) ...................................... 09 04912

(51) Int. Cl.
*G01N 21/64* (2006.01)
(52) U.S. Cl.
USPC ..................................................... 250/459.1
(58) Field of Classification Search
USPC ................................. 250/459.1, 458.1, 356.1
See application file for complete search history.

(56) References Cited

U.S. PATENT DOCUMENTS

| | | | | |
|---|---|---|---|---|
| 5,587,832 A | * | 12/1996 | Krause | 359/385 |
| 2004/0029152 A1 | * | 2/2004 | Ishida | 435/6 |
| 2008/0214913 A1 | * | 9/2008 | Van Gogh et al. | 600/318 |

OTHER PUBLICATIONS

Algar et al, "Towards multi-colour strategies for the detection of oligonucleotide hybridization using quantum tods as energy donors in fluorescencce resonance energy transfer (FRET)," 2007, Analytica Chimica Acta, vol. 581, pp. 193-201.*

* cited by examiner

*Primary Examiner* — Kiho Kim
(74) *Attorney, Agent, or Firm* — Bachman & LaPointe, P.C.

(57) ABSTRACT

An imaging system for analyzing fluorescent molecules in a sample, including a confocal microscope device, has a support in contact with at least a portion of the sample. In the system, the support surface in contact with the sample is functionalized so as to reduce the observation volume of the microscope on the surface in the axial direction. The present disclosure also relates to various uses of such a system as well as to a method for analyzing fluorescent molecules in a sample, the method being implemented by such a system.

12 Claims, 3 Drawing Sheets

IMAGING METHOD AND SYSTEM USING SUBSTRATE FUNCTIONALIZATION

BACKGROUND

1. Technical Field

The present invention relates to the field of the optical analysis (imaging and spectroscopy) of luminescent or optically diffusing particles.

It relates more particularly to an imaging system for analysing fluorescent particles in a sample, comprising a confocal or large-field microscopy device and comprising a support in contact with at least part of this sample. This imaging system finds its applications mainly in the implementation of a fluorescence correlation spectroscopy system, as well as the observation and study, in a biological medium, of the points of contact between a cell and the support of this imaging system.

It also relates to a sample support intended to equip such an imaging system, as well as to a method of analysing fluorescent molecules in a sample using such an imaging system.

2. Prior Art

A general technical problem in this field relates to the detection of individual molecules, whether by imaging in general or more specifically by fluorescence correlation spectroscopy (FCS). The molecules that are to be detected are fluorescent molecules, situated for example in a biological medium.

Detection of a single molecule generally requires the use of an ultrapure solvent (for example pure water) in order to reduce as far as possible the background noise due to the environment. However, these conditions of purity of the solution are never obtained in the case of experiments in an in vivo biological medium, for which the signal to noise ratio is considerably impaired by the existence of a background noise, mainly because of the autofluorescence phenomenon in these cells, as well as the Raman diffusion of the components and the cell environment.

This background noise depends on the size of the observation volume: the larger the observation volume, the greater the background noise, and vice versa.

Moreover, detecting individual molecules requires having a very large quantity of molecules in the observation volume, ideally a single molecule. Such observation conditions can be obtained using sufficiently diluted fluorophor solutions, but also by reducing the detection volume as far as possible.

Moreover, under conventional FCS conditions (i.e. on the basis of a confocal microscope) it is not possible to detect chemical species present at concentrations exceeding around 100 nanomols per liter (>100 nM). However, a large number of biological processes, such as enzymatic reactions, the expression of proteins or the action of medications, occur at concentrations of around 1 to 10 µM, or even more. Under these conditions, where the concentration of the molecules of interest becomes large, it then appears also necessary to considerably reduce the size of the observation volume, so as to make "visible" the fluctuations in the fluorescence signal and thus carry out the FCS. The same applies with the measurement of the diffusion time $T_d$. This is because those greater than a few hundreds of microseconds (>100 ms) are very difficult to measure by conventional FCS, mainly because of the photobleaching of the fluorescent sensors. Many processes, such as the diffusion of membrane proteins, or diffusion in dense heterogeneous media such as collagen, may take place very slowly. A significant reduction in the size of the observation volume makes it possible to access these extremely slow phenomena more easily.

All these constraints are therefore aimed at reducing the size of the observation volume, which also makes it possible to eliminate the background noise.

To achieve this aim, a confocal microscope may be used, advantageously having a lens with a large numerical aperture.

This is because the image of any object is limited by optical diffraction. The limit of resolution is directly correlated with the diffraction (diffraction limit is spoken of). This depends on the illumination wavelength ($\lambda$) and the numerical aperture of the optical system (ON), and is equal to approximately $\lambda$/ON. Under these conditions, in the visible range, the optimum lateral resolution (perpendicular to the optical axis of the microscope) in traditional microscopy is around 300 to 400 nm. However, the phenomenon of diffraction also limits the axial resolution (i.e. along the optical axis) of the microscope. Confocal microscopy constitutes at the present time the most conventional tool for tending towards this limit imposed by diffraction. It makes it possible to reduce the observation volume in the three directions in space. This technique is based solely on the use of a pinhole filter in detection. The observation volume limited by diffraction then has an elliptical form and is elongate along the optical axis. With lenses with a large numerical aperture (ON>1.2) the confocal observation volume is usually between 0.2 and 1 $\mu m^3$.

Under these conventional conditions (i.e. on the basis of a confocal microscope), FCS does not make it possible to detect chemical species present in concentrations exceeding around 100 nanomols per liter, nor to detect diffusion times greater than a few hundreds of milliseconds.

Consequently it appears necessary to reduce the size of the observation volume beyond what is offered by a microscope according to the prior art, so as to make the fluctuations in the fluorescence signal "visible" and thus to achieve an FCS measurement with greater precision.

Several solutions are known for addressing this problem of individual detection of molecules in a biological medium.

A first solution, a so-called STED technique, standing for "stimulated emission depletion", consists of using two femtosecond (or picosecond) laser sources that are synchronised. This near-field technique is based on an inhibition of the fluorescence signal via a computing relaxation method: stimulated emission. Stimulated emission is used to "trim" the periphery of the focusing spot of the exciting laser illumination, thus reducing the lateral and axial dimensions of the confocal volume.

Nevertheless, the complexity relating to the use of this type of light source and to the use thereof in microscopy makes this technique complex.

A second solution, a so-called STORM technique, standing for "stochastic optical reconstruction microscopy", or PALM standing for "photoactivated localisation microscopy", is based on a very precise localisation of the fluorescence signal of individual molecules observed by means of a conventional large-field microscope. Even if the image in far field of a single molecule is limited by diffraction (200-300 nm laterally and 600-800 nm axially), it is always possible to find the precise position of the molecule (i.e. the central position of the spot limited by diffraction). A new image representing the exact positions of the molecules can then be constructed, which makes it possible to display membrane proteins with very great precision.

However, this solution has the drawback of requiring excessively long acquisition times for envisaging dynamic studies, such as movements of proteins for example.

Thus, a certain number of novel techniques for reducing the confocal observation volume have been proposed. These techniques make it possible to carry out local spectroscopy based on the analysis of the fluctuations of the fluorescence signal of individual molecules by FCS.

Fluorescence correlation spectroscopy (FCS) is based on the evaluation of the temporal autocorrelation function $G_{AC}$(T) of the fluorescence signal F(t) emitted by molecules that pass through the optical detection volume:

$$G_{AC}(\tau) = \frac{\langle F(t)F(t+\tau)\rangle}{\langle F(t)\rangle^2} = \frac{\langle \delta F(t)\delta F(t+\tau)\rangle}{\langle F(t)\rangle^2} + l \text{ where} \quad (1)$$

$$\delta F(t) = F(t) - \langle F(t)\rangle$$

$\delta F(t)$ represents the fluctuations of the fluorescence signal (F(t) with respect to the mean signal <F(t)>.

According to equation (1), FCS is sensitive only to the fluctuations in the fluorescence signal, which are mainly related to the fluctuations in concentration of the molecules in the volume sounded. Nevertheless, these fluctuations may have several different origins and the physical processes that give rise to them occur to different timescales, FIG. 4.

In short times, typically less than 1 the change in $G_{AC}$(T), denoted G(T) in FIG. 4, is mainly governed by the internal dynamics of the fluorescent molecule (passage through the triplet state, rotation, etc.).

At long times, the physical process that governs the change in $G_{AC}$(T) is diffusion (Brownien motion or molecule flow). Then the amplitude of the autocorrelation function is inversely proportional to the number of molecules (<N>) contained in the observation volume; the decay time of $G_{AC}$(T) corresponds for its part to the average time that a molecule takes for diffusing through this volume. This time is called the diffusion time (denoted $T_d$ in FIG. 4).

To this it is also necessary to add the chemical reactions that may occur in the solution and modify the dynamics of the molecule studied (photobleaching, quenching, chemisorption, etc.).

The evaluation of <N> and of $T_d$ constitute the two types of measurement that offer a major interest in biophysics. This is because, after a first calibration step in order to estimate the size of the volume sounded, it then becomes possible for a person skilled in the art to deduce from <N> and $T_d$ the diffusion coefficient D and the concentration of the biomolecules of interest.

Among these recent techniques based on FCS, a third solution consists of using a microscope of the SNOM type (scanning near-field optical microscope), which is based on the use of a near-field optical microscope using evanescent waves. Local illumination of the sample takes place for example by means of a stretched metallised optical fibre. A "nanosource" of light is then obtained at the end of the fibre. Consequently, only the molecules present at the end will be excited.

Nevertheless, this technique proves equally complex to implement in a biological medium, for reasons' similar to those evoked in relation to the second solution above (STORM).

Another so-called nanohole technique, able to adapt to conventional fluorescence, makes it possible to reduce the size of the observation volume laterally and axially (with reference to the optical axis of the microscope), and to amplify the fluorescence signal. For this purpose holes of nanometric size are produced in a metal film. The excitation then remains confined in the hole.

The latter technique does not however make it possible to image an object in its entirety, such as living cells. The metal layer may modify the adhesion of the cells and in particular prevent any observation by means of a usual biology technique (phase contrast, DIC, RICM).

Thus, it appears that no solution of the prior art makes it possible to significantly reduce the dimensions of the observation volume (typically a few attoliters) in order to achieve local fluorescence spectroscopy and/or imaging, while making it possible to image, in a biological medium, a set of living cells with very low axial resolution (less than 10 nm).

In other words, at the present time there exists no simple solution to be implemented that can be compatible with conventional fluorescence observation, in order to avoid reconstructing a new FCS spectroscopy system while offering a reduction in the observation volume.

SUMMARY OF THE INVENTION

The aim of the present invention is to remedy this technical problem by modifying only the substrate (or support of the sample containing the living cells). For this purpose, the present invention is based on a novel architecture of the substrate serving as a support for the biological medium to be analysed, this novel architecture offering chemical functionalisation of the surface of the sample support.

More precisely, the subject matter of the present invention is an imaging system for analysing fluorescent molecules in a sample, comprising a confocal or large-field microscopy device comprising a support in contact with at least part of the sample. In this system, the surface of the support in contact with the sample is functionalised, which axially reduces the observation volume of the microscope at this surface.

Functionalisation, described more precisely below, enables the excitation of a sample not to be done directly with a focused laser source but via a transfer of non-radiative energy from nano-objects present on the surface of the substrate/support to fluorophors dispersed in the biological sample.

Unlike the prior art where the excitation of the fluorophors is done directly by a laser, according to the invention the excitation of the fluorophors is indirect, that is to say it is done by luminescent nano-objects (for example quantum dots), themselves previously excited by laser (or by electrical excitation).

Such a functionalisation of the surface of the support reduces the observation volume (i.e. collection volume) of the fluorescence emitted by the molecules in the medium to be analysed. Detecting the fluorescence of a smaller number of molecules is thus made possible, while maximising the signal to noise ratio.

In addition, this functionalisation of the surface of the (transparent) support scarcely modifies the transparency thereof, which makes it possible to produce images in phase contrast, DIC or RICM in a biological medium. In addition, this functionalisation proves to be inexpensive and does not require heavy equipment to be implemented.

Preferably, this functionalisation of the surface of the support consists of activating this surface so that the molecules at and close to it are excited via a transfer of non-radiative energy coming from previously excited luminescent nano-objects.

Consequently, by virtue of this activation, instead of directly exciting the sample with a focused laser source, excitation via a transfer of non-radiative energy at the surface of the support is made possible.

Preferably again, this activation of the surface of the support is obtained by at least partly coating it with a plurality of luminescent nano-objects arranged so that the energy of the nano-objects is transferred non-radiatively in the direction of the molecules present at and close to this surface.

These luminescent nano-objects are also called quantum dots. These nano-objects have a certain number of properties including, in comparison with fluorophors (i.e. fluorescent organic molecules), great photostability (little or no photobleaching at ambient temperature), and an intense luminescence signal.

A transfer of non-radiative energy (FRET) between these nano-objects and the fluorophors is effected. The quantum dot is the donor, the fluorophor the accepter. Chronologically, the donor absorbs the incident photons produced previously by a laser source at a first wavelength, in this case in the blue, and is then in an excited state. The FRET is then operated. The accepter, which was initially in its fundamental state, then goes into its excited state and can thus emit fluorescence photons by radiative relaxation. It is these fluorescence photons emitted at a second wavelength (different from the first), in this case towards the red, that are detected.

It is clear to a person skilled in the art that the FRET process is all the more effective, the smaller the distance between the quantum dot and the fluorophor. Typically, this phenomenon is no longer observed beyond a distance greater than 10 nm. Because of this, close to a surface functionalised by quantum dots, it is possible to create an excitation volume (which results at the time of the collection of the fluorescent light by an observation volume) defined by the range of the FRET, that is to say the depth of which does not exceed around ten nanometers.

Consequently, it appears that functionalisation by means of a coating of luminescent nano-objects offers the following advantages:
- selective detection (for selecting a single chemical species),
- dispensing with background noise, especially autofluorescence,
- detecting single molecules in a normal concentration range in living biology (a range of one micromole and more), and
- the possibility of studying diffusion in very viscous, dense and heterogeneous systems.

According to various particular embodiments, these luminescent nano-objects:
- are in the form of luminescent semiconductor nanocrystals,
- are spherical in shape.

According to a particular embodiment in which it is sought to map the presence of at least two different chemical species in the cell, provision can be made for the imaging system according to the invention to comprise at least two different types of luminescent nano-object arranged so that the respective energy thereof is transferred non-radiatively in the direction of fluorescent molecules present at and close to said surface and of different natures. That is to say the type of nano-object and the corresponding type of fluorophor are chosen so as to create as many donor-accepter pairs as there are chemical species to be analysed, selecting the respective emission/absorption spectra.

Advantageously, provision can also be made for the confocal or large-field microscopy device to be provided with:
- a focusing means arranged so as to collect the light generated by the fluorescence of the molecules at the focusing zone generated by said focusing means, and/or
- a spatial filtering means able to create an observation volume encompassing the FRET excitation volume of the molecules at said surface of the support in contact with said sample.

Another subject matter of the invention is the use of an imaging system as described above for implementing a fluorescence correlation spectroscopy system, the confocal or large-field microscopy device being provided with an illumination means able to emit an excitation light beam in the direction of the sample.

Another subject matter of the invention is the use of an imaging system as described above for determining the positions of the points of contact between a living cell and the system support.

Another subject matter of the invention is a sample support intended to equip the confocal or large-field microscopy device of an imaging system for analysing fluorescent molecules in a sample, so that the support is in contact with at least part of said sample. The surface of this support in contact with the sample has the particularity of being functionalised so as to axially reduce the observation volume of the microscope at said surface.

Finally, a subject matter of the invention is a method of analysing fluorescent particles in a sample by means of an imaging system, comprising a confocal or large-field microscopy device itself comprising a support in contact with at least part of the sample. This method is remarkable in particular in that the surface of the support in contact with the sample is previously functionalised so as to axially reduce the observation volume of the microscope at said surface.

The technique developed makes it possible to reduce an observation volume to nanometric dimensions, in this case an axial resolution ≤10 nm.

The present solution makes it possible to greatly reduce the size of an observation volume (typically a few attoliters) in order to perform local FCS, but also to image a set of living cells with an axial resolution less than or equal to 10 nm. It is based on a modification of the substrate on which the biological system to be studied (living cells) is deposited, that is to say it requires merely functionalising the glass surface that constitutes the bottom of the Petri dishes. No substantial microscope modification according to the prior art is required since the present solution is based solely on a novel architecture of the substrate/support, compatible with a conventional fluorescence observation, for example using a large-field or confocal microscope.

The present solution allows in particular the observation and study of points of adhesion between a cell and a substrate, and local fluorescence correlation spectroscopy, which are of interest in the field of biology/biophysics. A person skilled in the art will realise that the invention can be implemented also for any solute comprising fluorophors, for example in the field of chemistry.

BRIEF DESCRIPTION OF THE DRAWINGS

The invention will be understood more clearly from a reading of the detailed description of a non-limitative example embodiment, accompanied by figures showing respectively.

DETAILED DESCRIPTION OF THE PREFERRED EMBODIMENT(S)

Figure 1:
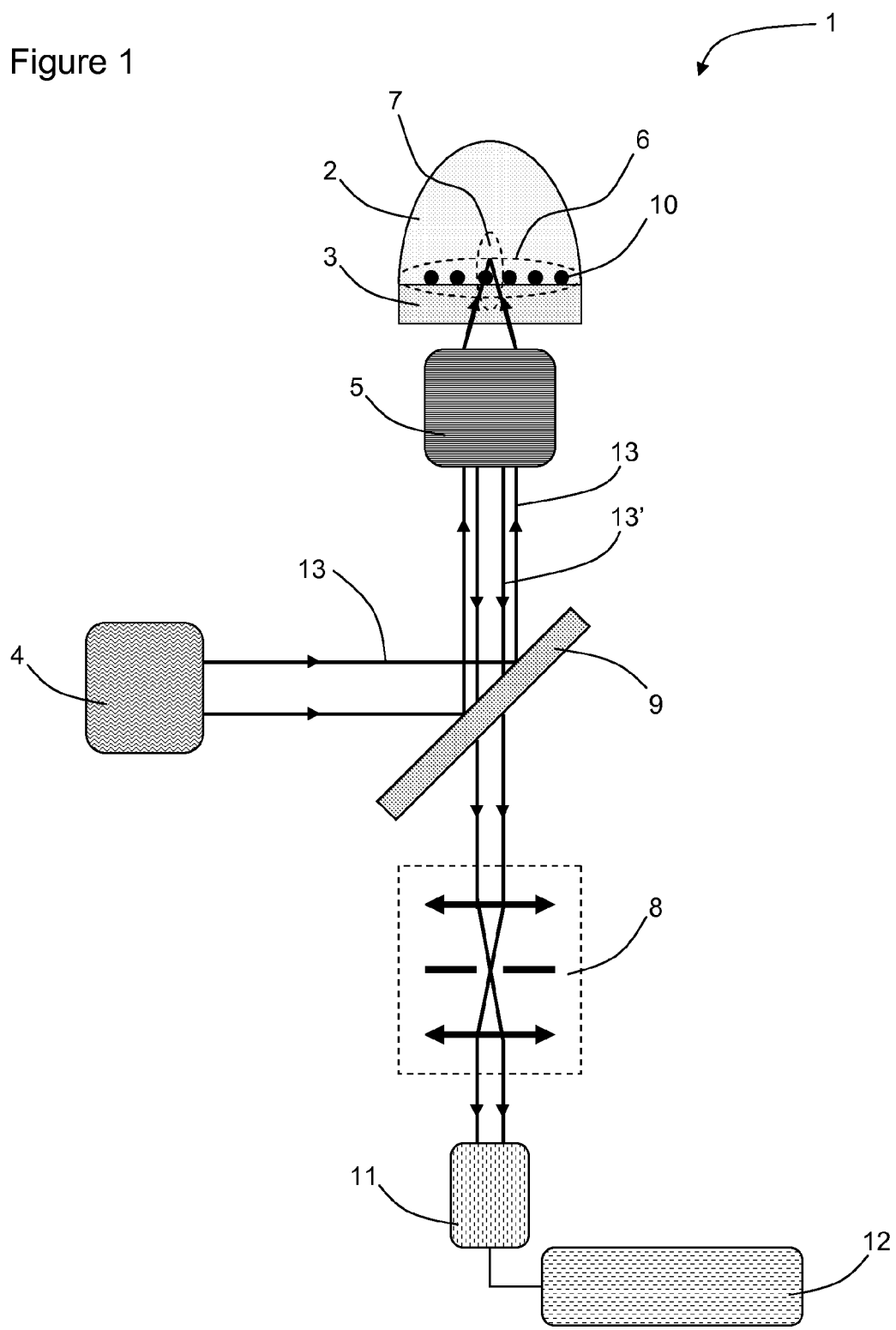
FIG. 1, a diagram of an imaging system according to the invention, used for implementing a fluorescence correlation spectroscopy system, FIG. 2, a diagram illustration the functionalisation of the support in the case of focused lighting, FIG. 3, a diagram illustrating the functionalisation of the support in the case of large-field lighting, FIG. 4, the changeover time of the autocorrelation function $G_{AC}(T)$ of the fluorescence signal F(t) emitted by the molecules passing through the optical observation space, and FIG. 5, typical absorption and emission spectra of a quantum dot and a fluorophor.

FIG. 1 shows a diagram of an embodiment of an imaging system, used for implementing a fluorescence correlation spectroscopy system.

This system is aimed at analysing a sample 2. This sample may be a fluid, liquid or gaseous medium or a biological object containing molecules to be analysed. The molecules to be analysed are molecules or molecular assemblies, for example molecular complexes, hereinafter referred to as "molecules", which comprise fluorophors and have nanometric dimensions, that is to say around a few nanometers to a few tens of nanometers, and preferably of the same order of magnitude as the Förster radius $R_0$.

This system, as in the prior art, comprises a microscopy device 1, in this case confocal. This microscopy device comprises a support 3, illumination means 4 (a light source), detection means 11 such as a sensor or photodetector, and means 12 of processing the signal received from the detection means 11. It may also comprise focusing means 5 such as a microscope objective or lens, dichroic separation means 9 such as a dichroic notch filter, and spatial filtering means 8 such as a spatial filter (pinhole).

The support 3 comprises, for example, a substantially flat glass substrate, such as a microscope plate or a dish bottom (in particular a Petri dish), preferably impervious, that is to say the lateral walls of which are formed by water-resistant self-adhesive shims. The sample 2 is deposited on the support 3.

The illumination means 4 emits an excitation light beam 13. This beam 13 is preferably collimated at the exit from the illumination means 4. The illumination means 4 comprises for example a laser source.

The excitation light beam 13 is directed to the dichroic separation means 9 (for example a dichroic notch filter), disposed for example at 45° to the incident excitation beam 13. The dichroic filter is configured so as, after reflection on it, to direct the excitation light beam 13 to the focusing means 5.

These focusing means 5 have a dual function. They make it possible firstly to direct the beam to a focusing zone, or observation zone 7, on the sample 2 through the microscopy system 1, in this case confocal in FIG. 1, and secondly to collect the fluorescence light intensity emitted by the molecules. These focusing means 5 comprise for example a microscope objective or lens, advantageously with a large numerical opening (for example 1.2) in order to collect an optimum fluorescence light intensity. These focusing means 5 can direct the beam, that is to say focus or concentrate it, either in a parallel fashion in large-field microscopy, or in a focused manner in confocal microscopy.

In the system proposed, a sample 2 is deposited on the support 3 deposited in the microscopy device 1.

Unlike the prior art, it is proposed to functionalise the support 3 so that it is coated at least partly with a plurality of luminescent nano-objects 10. These nano-objects, also referred to as quantum dots, are for example in the form of luminescent semiconductor nanocrystals, in particular, spherical in form.

The quantum dots 10 are preferably dispersed in a polymethylmethacrylate (PPMA) film deposited in a fine layer on the support 3 and the thickness of which is between 8 and nm (for a quantum dot thickness or diameter of approximately 7-8 nm), which guarantees the presence of a quasi-monolayer of quantum dots on the support 3.

These quantum dots 10, thus placed on the support 3, allow, when they are pre-excited, a non-radiative transfer of energy (FRET) with the fluorophors of the molecules of the sample 2 when they are close to the surface of the support 3, that is to say close to these quantum dots 10. Only the fluorescence photons generated by fluorophors close to these dots can be obtained. Consequently, only the fluorescence of the corresponding molecules can be detected.

It is in fact possible to carry out FRET ("Förster resonance energy transfer") between two species of different natures, in particular between quantum dots and fluorophors. Quantum dots, "Q-dots", are typically luminescent semiconductor crystals, of nanometric dimensions (typically 7-8 nm in diameter for spherical objects). These nanocrystals have a large number of properties, including, in comparison with a conventional fluorophor, great photostability (little or no photobleaching at ambient temperature) and an intense luminescence signal.

A non-radiative energy transfer goes between a quantum dot in its excited state D*, to a fluorophor in its fundamental state A. It is then said that the quantum dot is the "donor" and the fluorophor the "accepter". The energy transfer can then be written symbolically: D*+A→D+A*.

The donor (here the quantum dot) absorbs the incident photons produced by a laser source, in this case in the blue, and is then in its excited state D*. This is the phenomenon of pre-excitation. When the donor and accepter are at a distance from each other (that is to say below the radius of action of FRET of approximately 10 nm), the non-radiative transfer of the FRET type takes place: the fluorophor of the sample 2, which was initially in its fundamental state A, then goes into its excited state A* and can thus then emit fluorescence photons by radiative relaxation. It is these fluorescence photons, emitted in this case towards the red, that are detected, as described subsequently, by the detection means 11.

The de-excitation level relating to this non-radiative energy transfer is given by:

$$k_{F\ddot{o}rster} = \frac{1}{\tau_D}\left(\frac{R_0}{R}\right)^6 \propto \frac{\Phi_D}{\tau_D}\frac{I_R}{R^6} \quad (2)$$

where $T_D$ is the life span of the excited state of the donor in the absence of the accepter, R is the distance between donor and accepter. $R_0$ represents the Förster radius, that is to say the distance R separating the donor and the accepter for the efficacy of the transfer to be 50%. $R_0$ is typically around 5 to 10 nm. $k_{F\ddot{o}rster}$ can also be written as a function of the integral $I_R$ of overlap between the emission spectrum of the donor and the absorption spectrum of the accepter and the quantum yield $\Phi_D$ of the donor in the absence of the accepter. Expression (2) then shows that the FRET process is all the more effective, the higher the overlap integral $I_R$ and the smaller the quantum dot-fluorophor distance.

Figure 5:
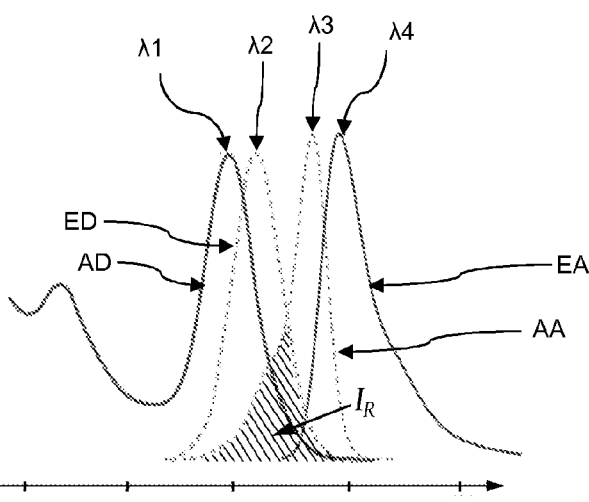

There is then a four-spectrum phenomenon, see FIG. 5, of absorption and emission for the donor and accepter respectively:

An absorption spectrum of the donor AD (quantum dot) is centred around a first wavelength $\lambda 1$, corresponding to the maximum wavelength of the illumination means 4, in this case blue laser.

The absorption of this energy by the quantum dots places them in their excited state. They are de-excited according to an emission spectrum ED of the donor centred around a second wavelength $\lambda 2$, such that $\lambda 2 > \lambda 1$.

An absorption spectrum of the accepter AA (fluorophor), centred around a third wavelength $\lambda 3$ and at least partially overlapping the emission spectrum ED of the donor (centred around $\lambda 2$), is such that $\lambda 3 > \lambda 2$.

The absorption of this energy by the fluorophors places them in their excited state. They are de-excited according to an emission spectrum of the accepter EA, centred around a fourth wavelength $\lambda 4$, such that $\lambda 4 > \lambda 3$.

It is preferably chosen to excite the donor in a wavelength range where the accepter does not absorb. The spectral shift between the laser excitation wavelength and the fluorescence emission of the accepter is then very great (typically 20 nm). Thus, by centring the spectral detection window on the emission of the accepter, it is possible to considerably reduce the background noise. The autofluorescence, the Raman and the direct excitation of the accepter then represent no more than a few % (5% to 10% maximum) of the total signal detected.

The functioning of the system is as follows: the excitation light beam 13, preferably focused, interacts with the fluorophors contained in the molecules in solution in the sample 2 not directly as in the prior art but by means of the quantum dots, via a non-radiative energy transfer. Each molecule in solution excited by a quantum dot emits, by fluorescence, a light response at a wavelength greater than that of the excitation beam 13 and that of the quantum dot 10. Part of this light response is then collected by the focusing means 5 so as to form a response light beam 13'.

This response light beam 13¹ is sent to the detection means 11 through the respectively focusing means 5, dichroic separation means 9 and spatial filtering means 8. The cut-off wavelength of the dichroic filter is chosen so as to transmit the response light beam 13', the wavelength of which is greater than that of the excitation beam 13.

In order to detect the response beam 13', the spatial filtering means 8 also comprises a set of lenses for combining the focal plane of the focusing means 5 with the sensor of the detection means 11. The spatial filtering means 8 also comprise an adjustable-dimension opening disposed on the optical axis of the system. It is combined optically with the focusing zone of the focusing means 5.

This spatial filtering means 8 makes it possible to select a detection volume—or spatial filtering volume, or confocal volume—around the focusing zone, since light rays not coming from this spatial filtering volume do not pass through the opening. The dimensions of the detection zone are correspondingly smaller along with those of the opening.

The detection means 11 makes it possible to measure the intensity of the response light beam 13' produced by interaction of the excitation beam 13 on the sample 2 by means of the quantum dots 10, and connected by the microscopy device, in this case confocal 1. This means 11 can comprise electron amplification photodetectors, such as photodiodes functioning in avalanche or cascade mode. These photodetectors may also be photomultipliers, optical amplification photodetectors or cooled CCD or CMOS cameras.

The signal issuing from the detection means 11 is sent to means 12 of processing the signal. This means 12 comprises for example a processor, a counter and a correlator and makes it possible to process the received data digitally. The counter records the value of the fluorescence light intensity received and the correlator carries out the temporal analysis of the fluctuations in the fluorescence light intensity received. This analysis can be done in short times and long times so as to obtain complementary information on the molecules in solution in the sample 2. At short times, the autocorrelation function of the light intensity detected makes it possible to have access to the photophysical parameters of the emitters and to the average number of molecules detected. At long times, this function gives information on the average residence time—the diffusion time—of the molecules and on their diffusion mode through the spatial filtering volume.

A reduction in the excitation volume then follows because of the presence of the quantum dots 10, and therefore a reduction in the observation volumes 7 of the microscopy device, corresponding to a confocal microscopy focusing zone, at a few nanometers from the surface, since only the fluorescence of the molecules close to the quantum dots 10 can be observed and therefore it will be possible to observe only the fluorescence of the molecules contained in a potential observation volume of the FRET phenomenon 6 delimited by the position of these dots and hereinafter referred to as FRET volume. This FRET volume 6 being limited in the axial direction (i.e. in the direction of the optical axis), the observation volume 7 is thereby reduced in the axial direction. The observation volume 7 of the microscopy device comprises all or part of the observation volume 6 of the FRET phenomenon.

It will immediately be clear to a person skilled in the art that any type of element (other than luminescent nano-objects) can be used in the context of the invention, insofar as these elements are liable to give rise to an excitation of the fluorophors in solution by FRET between these elements (donors) and the fluorophors (acceptors). Likewise, the form of these elements may be different from the spherical form described above.

A person skilled in the art will also note that the excitation of the luminescent nano-objects 10 can be achieved by light radiation or by any other excitation technique known in the field in question, for example by electrical excitation.

It is also possible to provide spectral filtering means so that only the photons emitted by the accepter (fluorophors) are detected by the sensor 11, for example a filter filtering the emission wavelengths of the donor (quantum dots).

Figure 2:
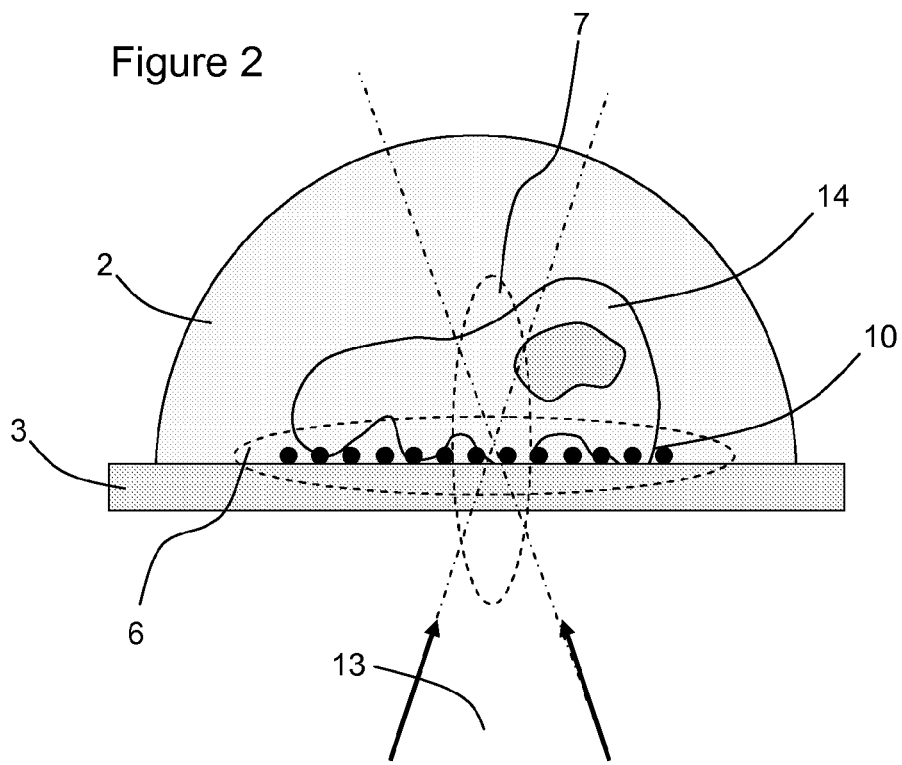
Figure 3:
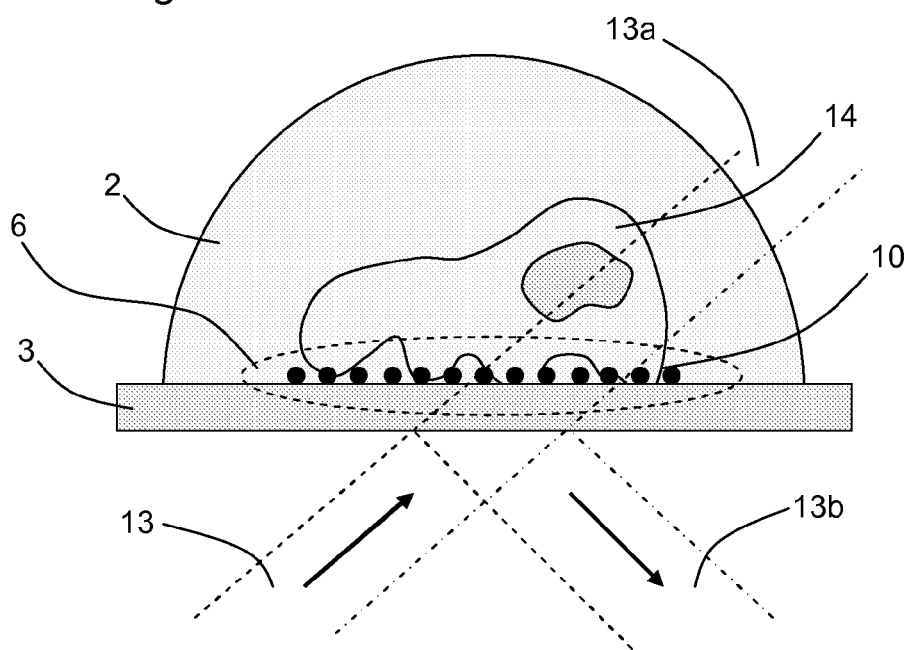
Figure 4:
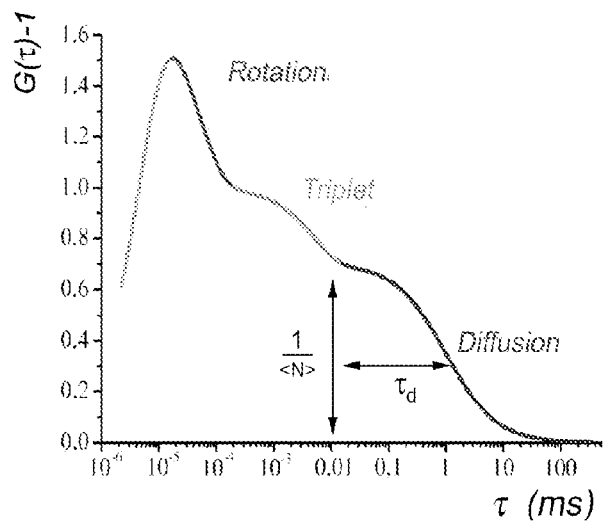

FIGS. 2 and 3 show diagrams of imaging systems according to embodiments of the invention, with illuminations respectively focused and large field.

In these two variants, it is sought to image a living cell 14 present in the biological medium 2. Quantum dots 10 are for this reason deposited on the substrate 3 so as to generate a non-radiative energy transfer in the direction of the fluorophors of the sample 2 over a small axial extent, represented by the FRET volume 6 delimited by broken lines.

With reference, to FIG. 2, a focused illumination 13 is effected, using suitable focusing means. The focusing point aimed at is situated at the top surface of the substrate 3, where the quantum dots 10 are disposed. A focusing spot is then obtained, corresponding to the observation volume 7 delimited by broken lines.

With reference to FIG. 3, a large-field illumination 13 is effected, using collimation means or the like. This illumination is aimed at part of the substrate 3, at a non-zero inclination vis-à-vis the perpendicular to the surface of this substrate. A part 13a or the like thus passes through the substrate, while another part 13b is reflected on its surface.

The non-radiative energy transfer occurs on each occasion in the zone delimited by the FRET volume 6, which makes it possible to image only the zone close to the substrate 3. The observation volume 7 is therefore thereby reduced axially. Among the possible applications of this type of embodiment, it is possible to image a living cell 14 so as to see which are the points of contact thereof with the substrate 3, which the imaging and/or spectroscopy systems known in the prior art did not permit up until then.

The advantages in using quantum dots as donors for FRET applications relate to the fact that the background noise produced firstly by the cells (autofluorescence and Raman) and secondly by the direct excitation of the acceptor are almost completely dispensed with.

By virtue of the present solution, the observation volume is no longer defined by the illumination zone of the laser beam (as according to the prior art) but by the efficacy zone of the FRET, typically given by the Förster radius $R_0$.

The invention claimed is:

1. Imaging system for analyzing fluorescent molecules in a sample, the system comprising said sample and a confocal or large-field microscopy device comprising a support in contact with at least part of said sample, a surface of the support in contact with said sample comprises luminescent nano-objects able to give rise to an excitation of the fluorescent molecules present in the sample by non-radiative energy transfer of a Forster type (FRET) when said nano-objects are previously excited.

2. Imaging system according to claim 1, wherein the luminescent nano-objects are previously excited by a light radiation or an electrical excitation.

3. Imaging system according to claim 2, wherein the luminescent nano-objects are previously excited by a laser light radiation emitting in blue.

4. Imaging system according to claim 1, wherein the luminescent nano-objects are luminescent semiconductor nanocrystals.

5. Imaging system according to claim 1, further comprising at least two types of different luminescent nano-objects arranged so that energies thereof are transferred non-radiatively in a direction of molecules present at and close to said surface and of different natures.

6. Imaging system according to claim 1, wherein the microscopy device is provided with illumination means able to emit a light beam, and provided with a focusing means arranged firstly so as to direct said light beam to the sample and secondly so as to collect fluorescence light intensity emitted by the fluorescent molecules present in the sample.

7. Imaging system according to claim 1, wherein the microscopy device is provided with a spatial filtering means able to create an observation volume encompassing the luminescent nano-objects present at said surface of the support and the fluorescent molecules present in the sample.

8. Use of an imaging system according to claim 1 for producing a fluorescence correlation spectroscopy system, having the confocal microscopy device being provided with an illumination means able to emit an excitation light beam in a direction of the sample.

9. Use of a large-field imaging system according to claim 1 for determining positions of points of contact between a living cell and the support of said system.

10. The imaging system according to claim 1, wherein said device is a confocal microscopy device, said nano-objects are excited, and fluorescence light intensity emitted by fluorescent molecules present in the sample are collected.

11. The imaging system according to claim 10, wherein the luminescent nano-objects are previously excited by light radiation or an electrical excitation.

12. The imaging system according to claim 10, wherein the luminescent nano-objects are previously excited by laser light radiation emitting in blue.

* * * * *